(12) United States Patent
Patton et al.

(10) Patent No.: US 8,732,879 B2
(45) Date of Patent: May 27, 2014

(54) PATIENT SUPPORT DEVICE

(75) Inventors: Phillip Patton, Windermere, FL (US);
Daniel Lowe, Las Vegas, NV (US);
William W. Orrison, Las Vegas, NV (US)

(73) Assignee: Worldwide Innovations & Technologies, Inc., Overland Park, KS (US)

( * ) Notice: Subject to any disclaimer, the term of this patent is extended or adjusted under 35 U.S.C. 154(b) by 273 days.

(21) Appl. No.: 12/705,950

(22) Filed: Feb. 15, 2010

(65) Prior Publication Data
US 2011/0200177 A1     Aug. 18, 2011

(51) Int. Cl.
*A47C 20/04*      (2006.01)

(52) U.S. Cl.
USPC ............... 5/640; 5/643; 5/644; 378/208

(58) Field of Classification Search
USPC ............ 5/601, 607, 630, 636, 637, 640, 643, 5/646, 652, 658, 614, 615, 632–634, 644, 5/655.3, 657; 378/208, 209, 20; 600/415; 128/845
See application file for complete search history.

(56) References Cited

U.S. PATENT DOCUMENTS

| | | | | |
|---|---|---|---|---|
| 2,120,310 A * | 6/1938 | Duncan | | 27/13 |
| 4,616,814 A * | 10/1986 | Harwood-Nash et al. | | 5/601 |
| 5,165,137 A | 11/1992 | Amrein et al. | | |
| 5,441,479 A | 8/1995 | Chitwood | | |
| 5,577,503 A * | 11/1996 | Bonutti | | 600/415 |
| 5,724,970 A * | 3/1998 | Votruba et al. | | 600/415 |
| 5,806,115 A * | 9/1998 | Brown | | 5/615 |
| 5,970,550 A * | 10/1999 | Gazes | | 5/715 |
| 6,138,302 A * | 10/2000 | Sashin et al. | | 5/600 |
| 6,151,737 A * | 11/2000 | Henninge | | 5/655 |
| 6,523,199 B2 * | 2/2003 | Gross | | 5/632 |
| 7,243,387 B2 * | 7/2007 | Schindler | | 5/601 |

* cited by examiner

*Primary Examiner* — Nicholas Polito
(74) *Attorney, Agent, or Firm* — Foley & Lardner LLP

(57) ABSTRACT

A device for supporting a patient during a radiological imaging procedure is disclosed. The device includes a base, a support member pivotally coupled to the base and configured to receive a portion of the patient undergoing the radiological imaging procedure and an adjustment device comprising an inflatable bladder. The inflatable bladder has a first portion acting on the base and a second portion acting on the support member. An inflatable state of the adjustment device is controllable to selectively adjust an angular positioning of the support member relative to the base.

24 Claims, 6 Drawing Sheets

PATIENT SUPPORT DEVICE

BACKGROUND

The present disclosure relates to a support device adapted for use during radiological imaging of a patient. More particularly, the present disclosure relates to a support device adapted to support the head and/or neck of a patient during radiological imaging using a Computed Tomography (CT) scanner.

CT scanners are commonly used to obtain cross-sectional images of the patient's body, including images of a patient's brain, lungs, heart, liver, bones, blood vessels, etc. CT scanners are often used to diagnose different kinds of diseases such as cancer, to plan radiation treatments and surgeries, and/or to guide physicians during biopsies or other invasive procedures.

During an imaging procedure, the portion of the patient's body that is to be imaged is often propped-up or elevated using a holder to support the body part in a desired position. Such holders are generally fixed devices configured to support a body part in only one position (e.g., a wedge-like pad or cushion, etc.). A problem arises when it may be desirable to take an image of the patient's body in different positions. For example, in the case of imaging a patient's spine, it may be desirable to obtain a first image of the patient's spine with the patient's neck and head tilted forward, a second image of the patient's spine with the patient's neck and head tilted back and/or a third image of the patient's spine with the patient's neck and head in a neutral position. Unfortunately, when using a fixed holder, the holder must be moved relative to the patient, interchanged with a holder of a different size or the patient must be reposition on the holder. Any such activity may be uncomfortable for a patient and/or may be burdensome on an operator performing the imaging procedure. Accordingly, it would be advantageous to provide a patient support device that can selectively move the patient into a number of different positions for imaging.

SUMMARY

An exemplary embodiment relates to a device for supporting a patient during a radiological imaging procedure. The device includes a base, a support member pivotally coupled to the base and configured to receive a portion of the patient undergoing the radiological imaging procedure and an adjustment device comprising an inflatable bladder. The inflatable bladder has a first portion acting on the base and a second portion acting on the support member. An inflatable state of the adjustment device is controllable to selectively adjust an angular positioning of the support member relative to the base.

Another exemplary embodiment relates to a device for supporting a patient during a radiological imaging procedure while on a patient table. The device includes a base configured to be position on top of the patient table, a support member pivotally coupled to the base and configured to receive a portion of the patient undergoing the radiological imaging procedure and an adjustment device comprising an inflatable bladder. The inflatable bladder has a first portion acting on the base and a second portion acting on the support member. An inflatable state of the adjustment device is controllable to selectively adjust an angular positioning of the support member relative to the base.

Another exemplary embodiment relates a method of adjusting a position of a portion of a patient undergoing a radiological imaging procedure. The method includes placing a patient support device on top of a patient table. The patient support device includes a base, a support member and an inflatable bladder for adjusting an angular position of the support member relative to the base. The method also includes placing the portion of the patient undergoing the radiological imaging procedure in the support member and controlling fluid pressure within the inflatable bladder to selectively rotate the support member relative to the base.

DETAILED DESCRIPTION

Referring generally to the FIGURES, a patient support device and components thereof are shown according to an exemplary embodiment. The patient support device may be used to support a portion of a patient undergoing radiological imaging, and is configured to selectively adjust the positioning of such portion so that the desired images can be obtained in a relatively efficient manner. According to the embodiment illustrated, the patient support device is a head support 10 configured to support the head and/or neck of a patient during the imaging (e.g., radiological imaging, etc.) of a patient's spine. While the patient support device is shown and described herein as a device configured to support the head and/or neck of a patient, the support device may be adapted for supporting other portions of a patient depending on the portion of the patient that is to be imaged (e.g., back, arms, legs, etc.). Further, the patient support device may find use in applications other than during radiological imaging procedures.

Figure 1:
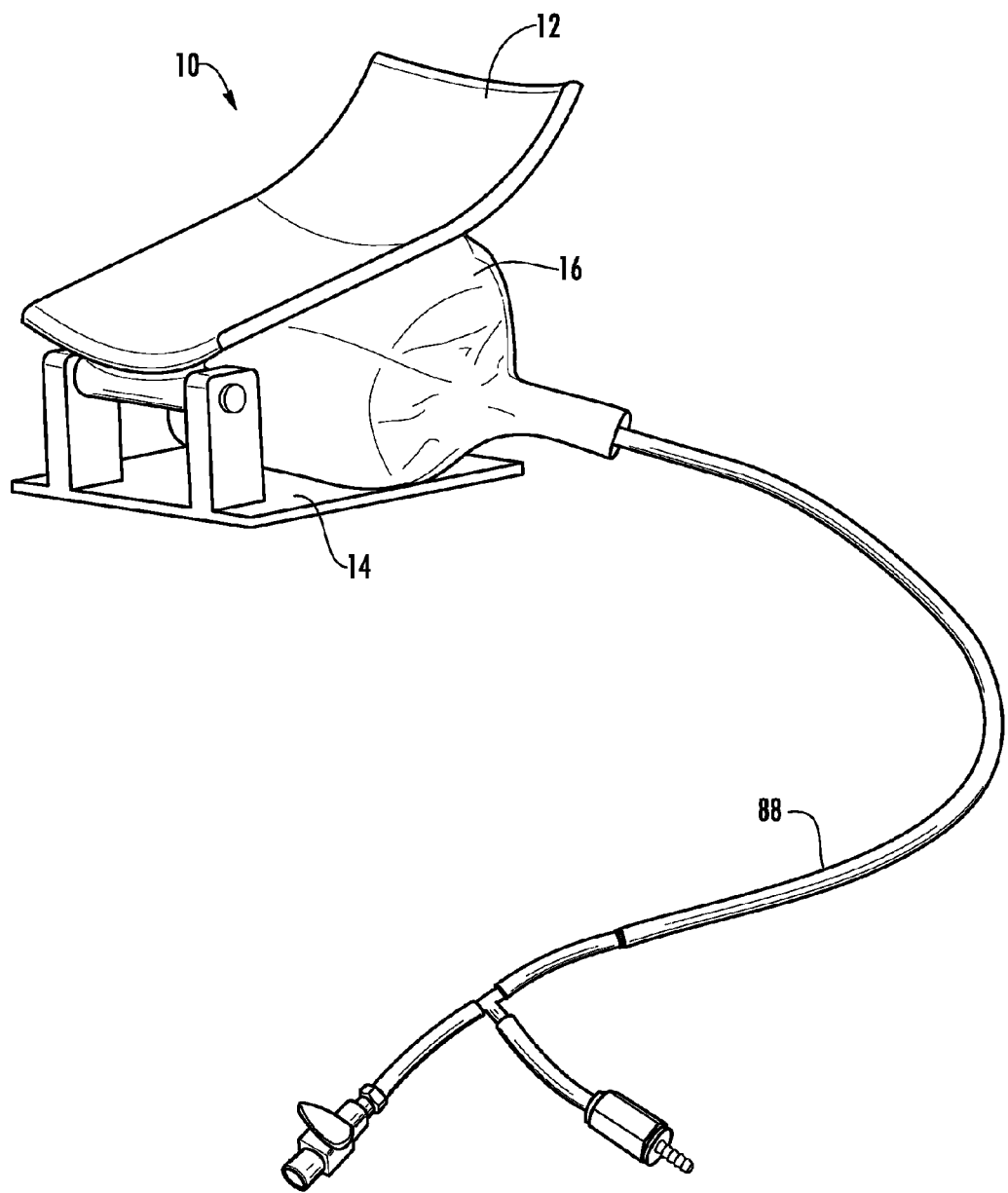
FIG. 1 is a perspective view of a patient support device according to an exemplary embodiment.

Referring to FIG. 1, head support 10 is shown as generally including a first portion (e.g., head piece, support member, etc.), shown as a head receiving portion 12, configured to support the head and/or neck of a patient and a second portion (e.g., stand, support frame, etc.), shown as a base portion 14, configured to support head receiving portion 12 in a manner that permits the positioning of head receiving portion 12 to be selectively changed (e.g., reconfigured, etc.). Head support 10 also includes a mechanism (actuator, adjuster, etc.), shown as an adjustment device 16, configured to adjust the positioning (e.g., orientation, etc.) of head receiving portion 12 relative to base portion 14 and/or a structure upon which a patient is supported. Head support 10 may further include a control device that allows an operator (e.g., the medical personnel performing the imaging procedure, etc.) to selectively control adjustment device 16, and thus, the positioning of head receiving portion 12 relative to base portion 14.

Figure 2:
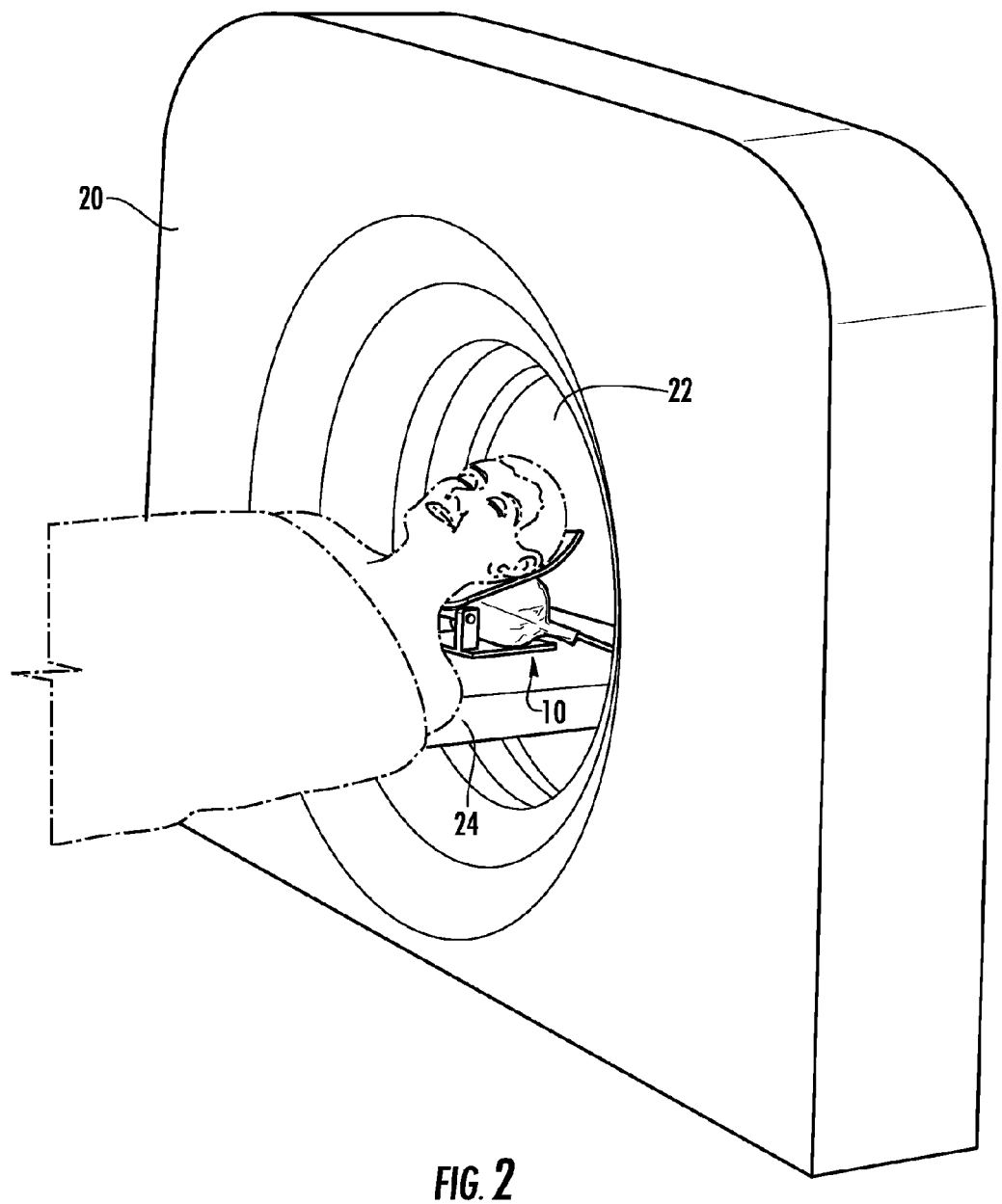
FIG. 2 is a partial cross sectional view showing the patient support device being used with a Computed Tomography machine.

Referring to FIG. 2, head support 10 is shown as being used with a Computed Tomography (CT) machine 20 of the type commonly used to create cross-sectional images of a patient. The configuration of CT machine 20 is provided for exemplary purposes only and is not intended to be limit the types of devices that head support 10 may be used in combination with. CT machine 20 includes a housing that encloses a support structure, referred to as gantry, that is configured to support at least one x-ray emitter and at least one x-ray detector. The gantry defines an opening 22 in which at least a portion of the patient, supported on a patient table 24, is inserted. Patient table 24 is generally positioned perpendicular to a front wall of housing and may be movable in the vertical and horizontal directions relative to opening 22 as well as transversely. To obtain an image, the patient is placed on patient table 24 and is positioned between the x-ray emitter and the x-ray detector. A primary beam of x-ray radiation emanating from the x-ray emitter passes through the patient before being captured by the x-ray detector. According to the various alternative embodiments, head support 10 may be used with any other type of imaging device.

Figure 5:
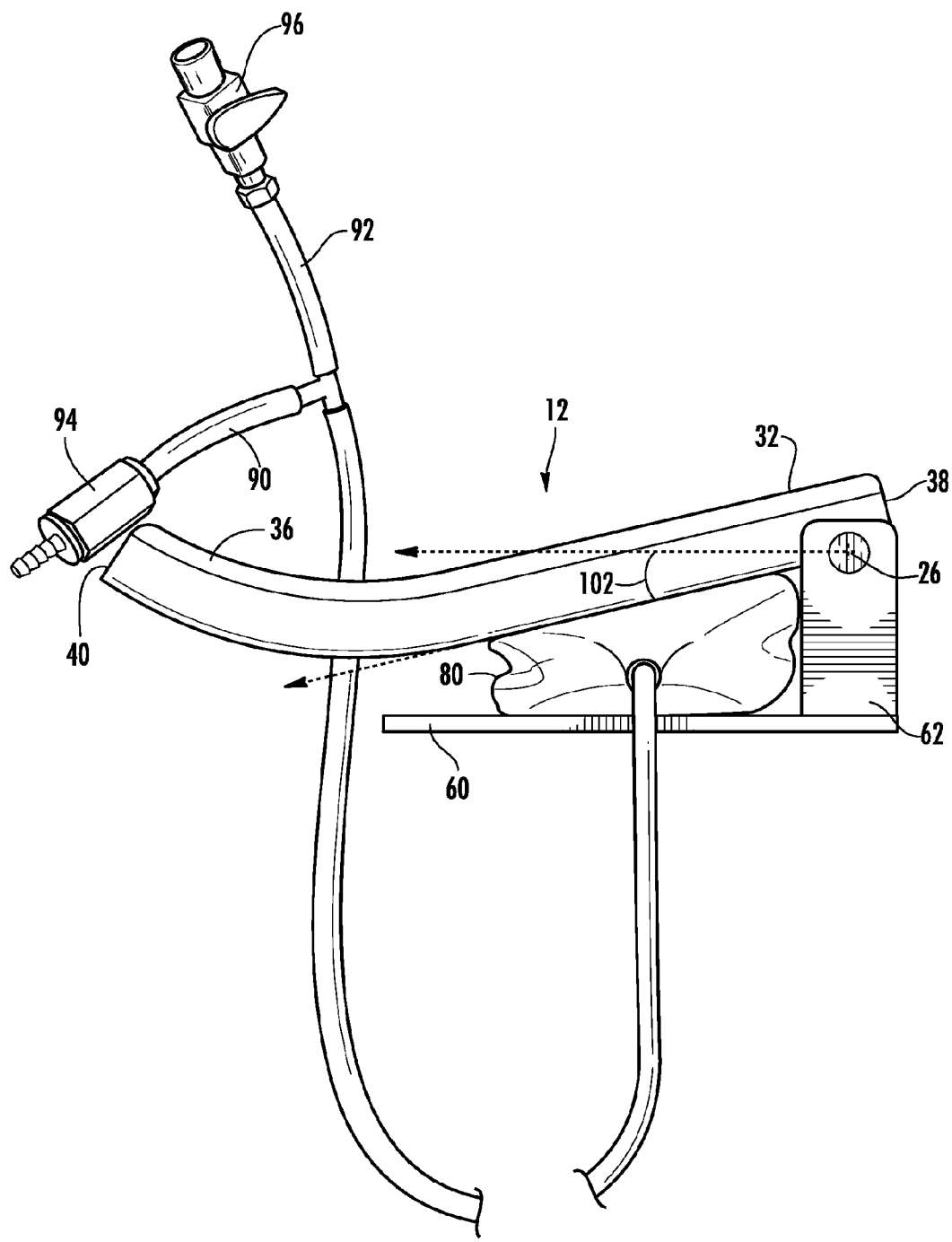
FIG. 5 is a side elevation view of the patient support device in a second position.
Figure 6:
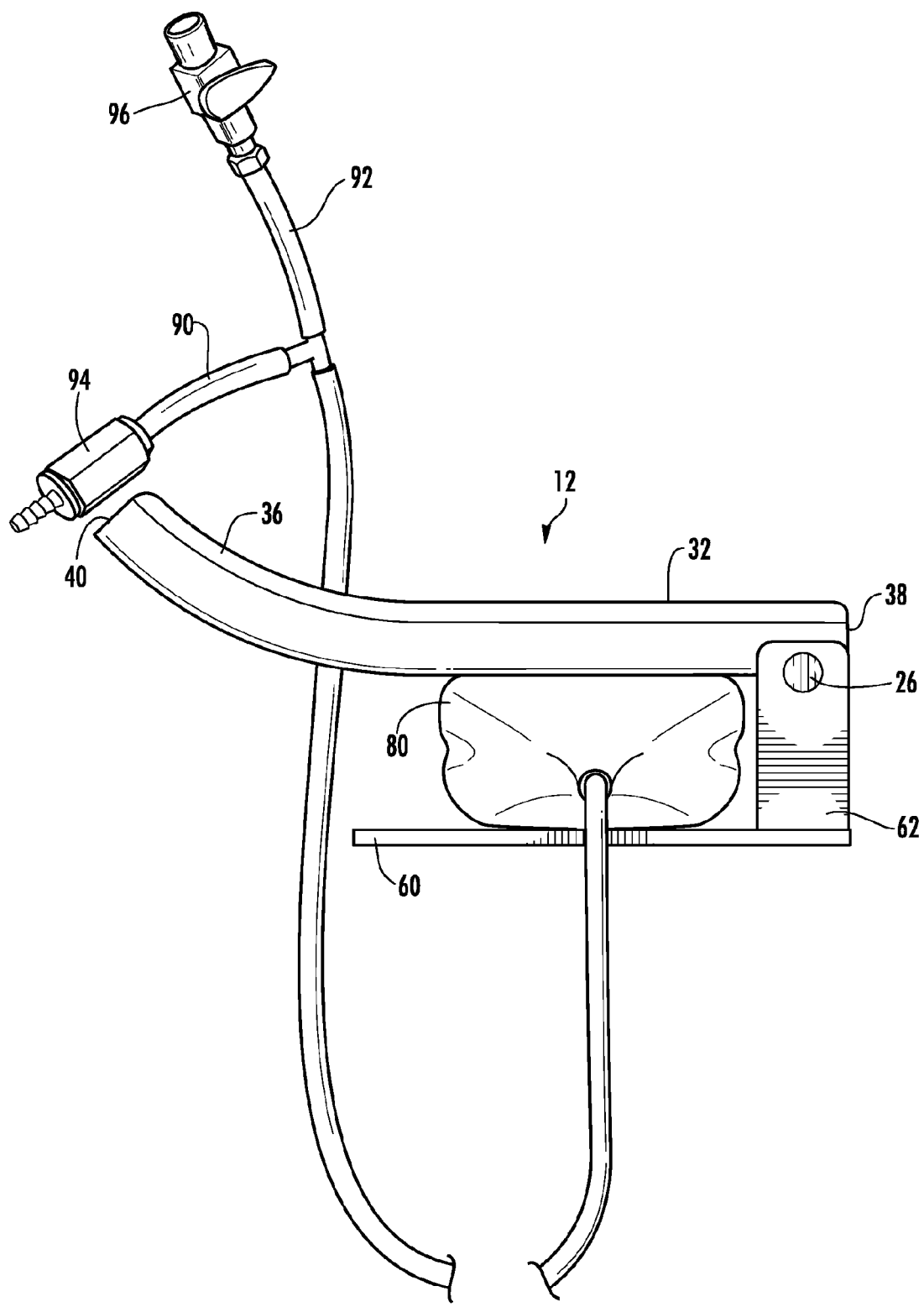
FIG. 6 is a side elevation view of the patient support device in a third position.

As can be seen in FIG. 2, head support 10 is configured to be supported on top of patient table 24. With head support 10 on patient table 24, and the neck and head of the patient resting on head support 10, head receiving portion 12 is configured to be moved between a plurality of positions relative to base portion 14. For example, in FIG. 4, head receiving portion 12 is shown as being supported at an orientation that is configured to be angled upwardly relative to a plane defined by patient table 24. In FIG. 5, head receiving portion 12 is shown as being supported at an orientation that is configured to be angled downwardly relative to the plane defined by patient table 24. In FIG. 6, head receiving portion 12 is shown as being supported at an orientation that is configured to be supported at an orientation that is substantially parallel to patient table 24 (e.g., a horizontal position, etc.).

According to an exemplary embodiment, head support 10 is selectively moved between the various positions by rotating head receiving portion 12 relative to base portion 14 about a pivot shaft defining an axis 26. According to an exemplary embodiment, axis 26 is configured to extend substantially perpendicular to the spine of the patient and parallel to the frontal plane of the patient when the patient is lying on his or her back on patient table 24. By rotating head receiving portion 12 relative to base portion 14, the patient's spine can be imaged in a variety of positions.

Figure 3:
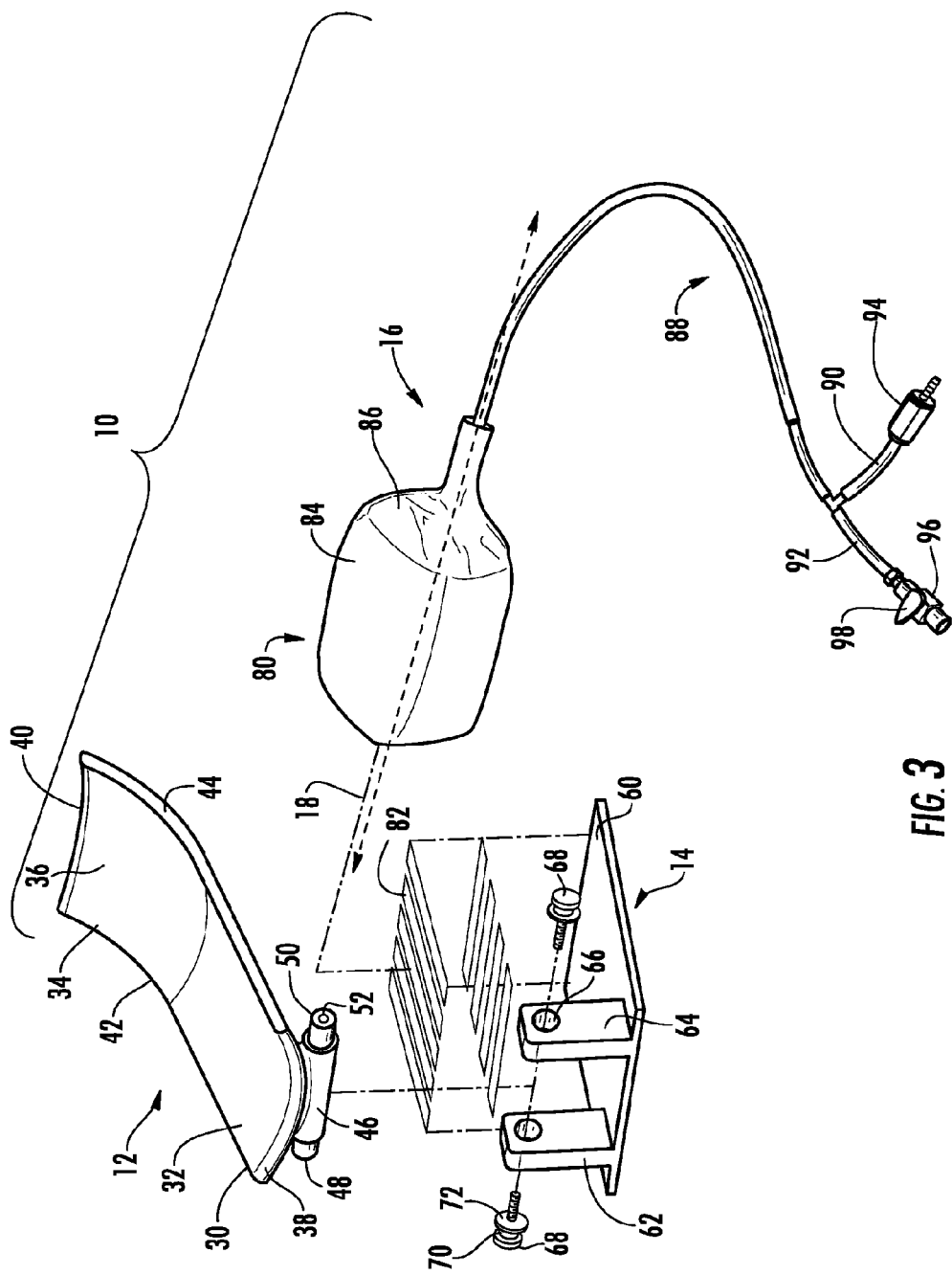
FIG. 3 is an exploded view of the patient support device.

Referring to FIG. 3, head receiving portion 12 is shown according to an exemplary embodiment. Head receiving portion 12 includes a lower portion 30 having a support surface 32 that is configured to support and/or underlie the neck of the patient and an upper portion 34 having a support surface 36 that is configured to support and/or underlie the rear head area of the patient. According to an exemplary embodiment, lower portion 30 and upper portion 34 are integrally formed as a one-piece unitary body and support surfaces 32, 36 cooperate to provide a substantially continuous surface for the patient. According to the embodiment illustrated, the neck and head of the patient are configured to be supported directly on support surfaces 32, 36. According to the various alternative embodiments, a cushioned or padded layer (e.g., a foam pad, etc.) may be provided on one or more support surfaces 32, 36 to provide additional comfort for the patient.

Figure 4:
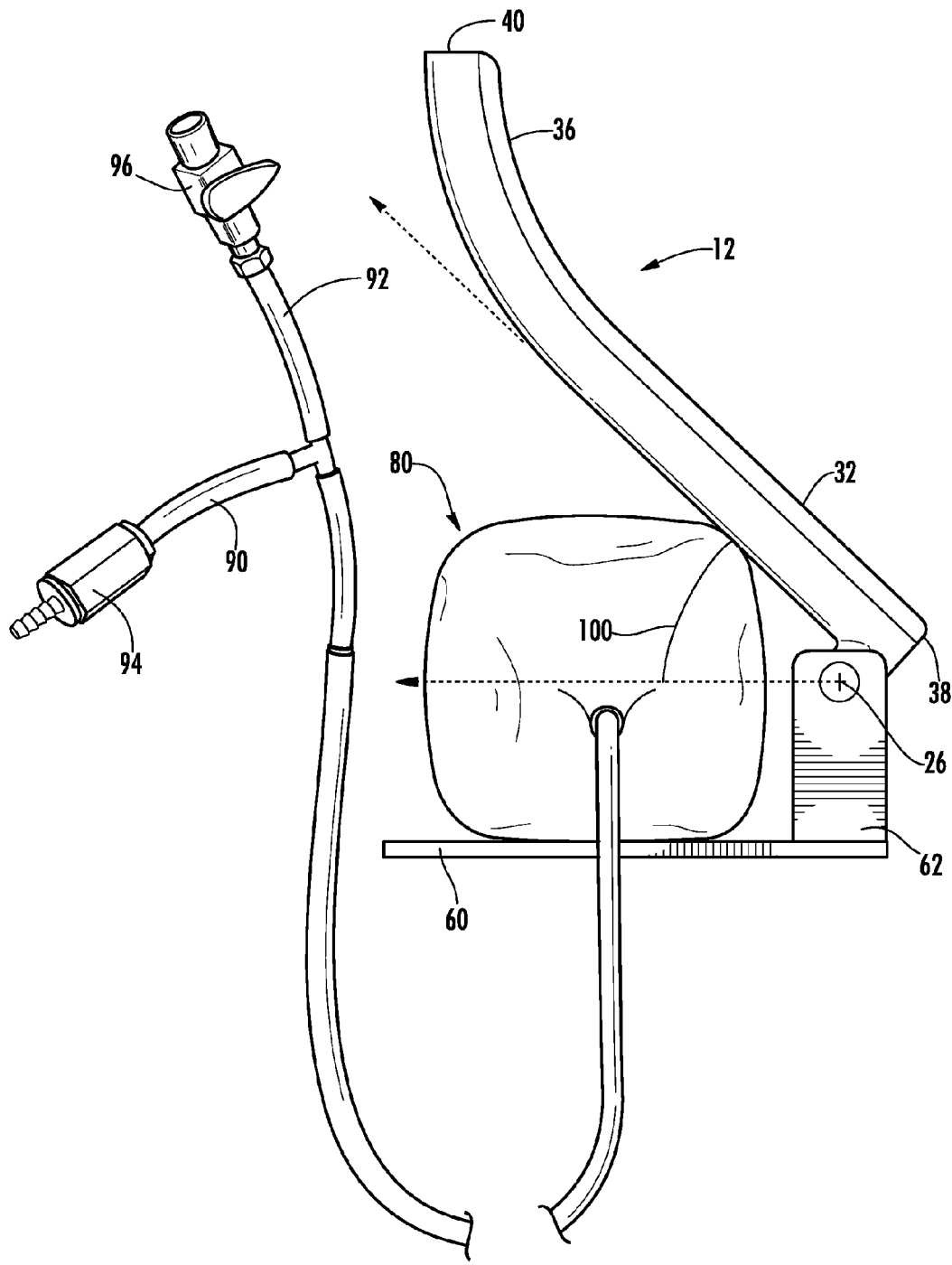
FIG. 4 is a side elevation view of the patient support device in a first position.

Referring to FIG. 4, head receiving portion 12 is shown as curving upwards as it extends from lower portion 30 to upper portion 34. According to the embodiment illustrated, lower portion 30 extends in a substantially linear manner starting at a first or bottom end 38 and extending towards upper portion 34. In such an embodiment, upper portion 34 curves upwards, at a substantially constant radius, starting at its transition with lower portion 30 and extending towards a second or upper end 40. While such a support profile is believed to be desirable in terms of patient comfort and for obtaining the desired images, the profile may be otherwise optimized for the particular application in which the patient support device is being used. For example, the radius of upper portion 34 may be variable or, alternatively, upper portion 34 may be substantially linear. Also, lower portion 30 may include one or more portions that extend in a curvilinear manner. Further, while the support profile defined by support surfaces 32, 36 is shown as being substantially the same as the overall profile of lower portion 30 and upper portion 34, according to the various alternative embodiments, the overall shape of lower portion 30 and upper portion does not have to follow that same profile as support surface 32, 36. With regard to patient comfort, the relevant profile is the support profile defined by support surfaces 32, 36. The back or bottom surfaces of lower portion 30 and upper portion 34 may have any of a variety of profiles. For example, the back surfaces may have a profile configured to optimize the interaction between head receiving portion 12 and adjustment device 16.

According to an exemplary embodiment, head receiving portion 12 is configured to cradle the neck and/or head of the patient from a lateral or side-to-side perspective. As shown in FIG. 1, lower portion 30, and particularly support surface 32, is concave as it extends between a first lateral side 42 (e.g., a left side, etc.) of head receiving portion 12 and a second lateral side 44 (e.g., a right side, etc.) of head receiving portion 12. While lower portion 30 is shown as extending laterally at a substantially constant radius, the radius may vary across the width of lower portion 30. According to the embodiment illustrated, that same concave profile is continued along upper portion 34, and particularly support surface 36, so head receiving portion 12 provides a gently curved surface on which the neck and head of the patient can rest. Once again, such a support profile is believed to be desirable in terms of patient comfort and for retaining the patient in the desired position. According to the various alternative embodiments, only the side margins of support surfaces 32, 36 may curve upwardly, while the central portions remain substantially flat. According to still further alternative embodiments, one or more of support surfaces 32, 36 may remain substantially flat in the lateral direction.

Referring back to FIG. 3, head receiving portion 10 is also shown as including a mounting structure (e.g., connector, support member, etc.), shown as a projection 46, provided at bottom end 38. Projection 46 is shown as being centrally portioned at bottom end 38 and extending downward from the back surface of lower portion 30. According to the embodiment illustrated, projection 46 has a substantially circular cross section and extends in a lateral direction between a first end 48 and a second end 50. The diameter of projection 46 at first end 48 and second end 50 is reduced or necked down relative to the main portion of projection 46. As detailed below, the reduced diameters of first end 48 and second end 50 configured to be received within a corresponding mounting structure provided on base portion 14 in a manner that along head receiving portion 12 to rotate relative to base portion 14. First end 48 and second end 50 are also each shown as including an aperture 52 configured to receive a fastener (e.g., a screw, locking pin, clip, etc.) that secures head receiving portion 12 to base portion 14.

According to an exemplary embodiment, head receiving portion 12 is integrally molded as a one-piece unitary member. Head receiving portion 12 is formed of a material that is substantially radiolucent so that head support 10 will not adversely affect the image quality of the x-ray images taken by the CT scanner or other imaging device (e.g., will reduce the likelihood of streaking artifact, etc.). According to an exemplary embodiment, head receiving portion 12 is formed of an acrylonitrile butadiene styrene (ABS) plastic, but alternatively may be formed of any suitable plastic material (e.g., a polycarbonate plastic, etc.) or non-plastic material that is substantially radiolucent. It should also be noted that, although head receiving portion 12 is shown as being formed as a one-piece member, head receiving portion 12 may be formed of separate members that are subsequently coupled together, for example by adhesive or by mechanical fasteners such as screws. For example, any one of lower portion 30, upper portion 34 and projection 46 may be formed as a separate member that get connected to form head receiving portion 12.

Still referring to FIG. 3, base portion 14 is shown according to an exemplary embodiment. Base portion 14 is configured to support head receiving portion 12 in a manner that permits the positioning of head receiving portion 12 to be selectively changed. According to an exemplary embodiment, base portion 14 includes a base, shown as a platform 60, that is configured to support the weight of head support 10 and to stabilize head support 10 during use. According to the embodiment illustrated, platform 60 is a substantially rectangular member having a bottom surface that is substantially flat. Providing platform 60 with a substantially flat bottom surface allows platform 60 to be readily placed upon patient table 24 or other support structure for the patient. A frictional surface may be added to the bottom surface (e.g., rubber pads or feet, etc.) to reduce the likelihood that head support 10 will slide around after being positioned on patient table 24. To further reduce the likelihood that head support 10 will slide during use, platform 60 is sized to receive a coupling device (e.g., a clamp, a support bracket, etc.) for securing head support 10 to patient table 24. According to an exemplary embodiment, an effort is made to minimize the overall footprint of platform 60 so that head support 10 can be portable (e.g., sized so that medical personnel can easily add or remove from the patient table and store it when not in use, etc.).

Base portion 14 also includes a mounting structure, shown as two projections 62 and 64, for coupling head receiving portion 12 to base portion 14. Projections 62 and 64 support head receiving portion 12 so that head receiving portion 12 is pivotally movable with respect to base portion 14 about axis 26 which normally extends generally horizontally transversely and below the neck area of the patient. Such a configuration allows head receiving portion to pivot about axis 26 so that the angular positioning of head receiving portion 12 can be varied for the particular examination or treatment being performed.

According to the embodiment illustrated, projections 62 and 64 are provided at a front end of platform 60 (e.g., the end of platform 60 that is configured to be positioned under the neck of a patient, etc.) and are disposed adjacent and outwardly of respectively opposite sides of projection 46. Projections 62 and 64 each define a substantially circular opening or bore 66 configured to receive first end 48 and second end 50 of projection 46. When received within bores 66, first end 48 and second end 50 function as a pivot shaft defining axis 26 about which head receiving portion 12 rotates relative to base portion 14.

According to an exemplary embodiment, first end 48 and second end 50 turn within bores 66 as the angular position of head receiving portion 12 is rotated about the axis. The diameter of bores 66 is substantially the same as the diameter of first end 48 and second end 50 so that first end 48 and second end 50 can rotate in a generally smooth manner within bores 66. When assembled, first end 48 and second end 50 of projection 46 pass through bores 66 until they are substantially flush with an outer surface of projections 62 and 64 respectively. In such a configuration, the width of projections 62 and 64 is substantially the same as the length of first end 48 and second end 50.

Projections 62 and 64 are shown as extending upward from platform 60 in a substantially vertical direction. According to an exemplary embodiment, the height of projections 62 and 64 and the positioning of bores 66 is sufficient to allow head receiving portion 12 to rotate through a desired range of movement relative to base portion 14.

First end 48 and second end 50 of projection 46 are secured to base portion 14 by fasteners, shown as screws 68 which extend through projections 62 and 64 and into first end 48 and second end 50. According to an exemplary embodiment, one or more spacers 70 and/or washers 72 are provided at each end to ensure that head receiving portion 12 is coupled to base portion 14 is a secured manner. Spacers 70 and/or washers 72 may also ensure smooth pivotal movement of head receiving portion 12 relative to base portion 14.

According to an exemplary embodiment, base portion 14 is integrally formed as a one-piece unitary body. Similar to head receiving portion 12, base portion 14 is formed of a material that is substantially radiolucent so that head support 10 will no adversely affect the image quality of the x-ray images taken by the CT scanner or other imaging device. According to an exemplary embodiment, base portion 14, like head receiving portion 12, is formed of an acrylonitrile butadiene styrene (ABS) plastic, but alternatively may be formed of any suitable plastic material (e.g., a polycarbonate plastic, etc.) or non-plastic material that is substantially radiolucent. While base portion 14 is shown as being formed as a one-piece member, base portion 14 may be formed of separate members that are subsequently coupled together, for example by adhesive or by mechanical fasteners such as screws. For example, projections 62 and 64 may be formed separately from platform 60.

To facilitate the selective movement of head receiving portion 12 relative to base portion 14, adjustment device 16 is provided. According to an exemplary embodiment, adjustment device 16 comprises an inflatable bladder 80 (e.g., bag, pouch, etc.). Inflatable bladder 80 is shown as being provided between head receiving portion 12 and platform 60. The state of inflation of inflatable bladder 80 is selectively controllable to adjust the position of head receiving portion 12 relative to base portion 14 at any position between an extended position (shown in FIG. 4) and a compressed position (shown in FIG. 5).

According to an exemplary embodiment, inflatable bladder 80 includes a first portion configured to directly engage the back surface of head receiving portion 12 and a second portion configured to directly engage a top surface of platform 60. According to the embodiment illustrated, the second portion of inflatable bladder 80 is coupled to platform 60 using a fastener, shown as a hook and loop fastener 82, so that inflatable bladder 80 remains fixed to base portion 14 while the state of inflation is changed.

According to an exemplary embodiment, inflatable bladder 80 is an elongated member that defines a longitudinal axis 81. According to the embodiment illustrated, axis 81 is configured to be substantially parallel to axis 26 about which head receiving portion 12 is configured to pivot. In such an embodiment, a side wall portion 84 of inflatable bladder 80 is configured to engage head receiving portion 12 and base portion 14, while an end wall portion 86 of inflatable bladder 80 defines an opening that allows fluid to enter and exit inflatable bladder 80.

Inflatable bladder 80 is supplied with fluid through a fluid conduit system 88. Fluid conduit system 88 includes a fluid supply line 90 and a fluid outlet line 92. Fluid under pressure, preferably air, is supplied to inflatable bladder 80 through fluid supply line 90 via a pump or a high pressure air line as is commonly found in medical environments. A first control mechanism, shown as a check valve 94, is provided in fluid supply line 90. Check valve 94 allows the pressurized fluid to reach inflatable bladder 80, but is configured to prevent fluid from moving back towards the fluid source. Upon inflation of inflatable bladder 80, inflatable bladder 80 expands thereby rotating head receiving portion 12 upwardly about the axis defined by first end 48 and second end 50 of projection 46. According to the embodiment illustrated, it is the expansion of inflatable bladder 80 in the radial direction that causes head receiving portion 12 to move. According to the various alternative embodiments, inflatable bladder 80 may be repositioned or oriented relative to base portion 14 so that it is the expansion of inflatable bladder 80 in the axial direction that causes head receiving portion 12 to move.

Similarly, upon the reduction of pressure in inflatable bladder 80, inflatable bladder 80 compresses thereby lowering head receiving portion 12 relative to body portion 14. The state of inflation of inflatable bladder 80 is selectively controllable using a second control mechanism, shown as a release valve 96, provided in fluid outlet line 92. Release valve 96 includes a user interface (e.g., handle, etc.), shown as a lever 98, configured to be actuated by medical personnel to adjust the fluid pressure within inflatable bladder 80, thereby adjusting the angular positioning of head receiving portion 12.

When inflatable bladder 80 is in a neutral condition, lower portion 30 of head receiving portion 12 is shown as being supported at a substantially horizontal orientation that is parallel with platform 60 and/or the patient table. When inflatable bladder 80 is inflated, head receiving portion 12 is rotated upwardly about axis 26. When inflatable bladder 80 is deflated (e.g., by at least partially opening release valve 96), head receiving portion is rotated downwardly about axis 26. Again, by controlling the pressure in inflatable bladder 80, the operator can fix head receiving portion at any given position within its range of motion, in order to image the spine at a selected degree or flexion of extension.

According to an exemplary embodiment, inflatable bladder 80 is formed of a material that is substantially radiolucent so that head support 10 will no adversely affect the image quality of the x-ray images taken by the CT scanner or other imaging device. According to an exemplary embodiment, inflatable bladder 80 is formed of a polyethylene terephthalate (PTPE) plastic or rubber material. According to the various alternative embodiments, inflatable bladder 80 may be formed of any other suitable radiolucent material. Further, according to the embodiment illustrated, a cover, also formed of a substantially radiolucent material at least partially encloses inflatable bladder 80. The cover protects inflatable bladder 80 and may also provide a surface or structure for coupling adjust device 16 to base portion 14.

The operation of head support 10 will now be described with reference to FIGS. 2 and 4 through 6. With a patient lying on patient table 24, the neck and head of the patient is received with head receiving portion 12 of head support 10. If head receiving portion 12 is maintained in the position shown in FIG. 6, the neck of the patient can be imaged in a substantially flat position. If head receiving portion 12 is moved to a raised position, as shown in FIG. 4, the neck of the patient can be imaged in an extended or hyper-extended condition. If head receiving portion 12 is moved to a lowered condition, as shown in FIG. 5, the neck of the patient can be imaged in a flexed or hyper-flexed condition.

To selectively move and lock the inflation state of inflatable bladder 80 in the desired position, the operator activates the fluid supply and/or actuates release valve 96 depending on which position is desired. To raise the head of a patient (i.e., to rotate head receiving portion 12 upwardly), the operator activates the fluid supply so that pressurized fluid enters inflatable bladder 80 and causes it to expand. As inflatable bladder 80 extends, side wall 84 engages the back surface of head receiving portion 12 and causes it to rotate upwardly. Once the desired position is achieved, the operator can turn off the fluid supply and can close release valve 96 to maintain head receiving portion in the desired position. To lower the head of the patient (i.e., to rotate head receiving portion 12 downwardly), the operator can at least partially open release valve 96 which will cause inflatable bladder 80 to deflate. Once the desired position is achieved, the operator can once again close release valve 96.

Because the inflation state of inflatable bladder 80 is selectively controllable and lockable at any state of inflation, the neck of the patient can be imaged when in any selected orientation within the full range of motion of head receiving portion 12. Accordingly, head support 10 provides an apparatus for imaging the neck of a patient, at any selected one or group of a plurality of orientations, without any extra effort on the part of the patient.

According to an exemplary embodiment, head receiving portion 12 is configured to be adjusted between a range of movement that is between an inclination of approximately 45 degrees over horizontal (as shown in FIG. 4 as angle 100) and an inclination of approximately 25 degrees below horizontal (as shown in FIG. 5 as angle 102). According to the various alternative embodiments, this range of movement made be exceeded or decreased depending on the particular application in which head support 10 is going to be used. The range of movement may be controlled by the size of inflatable bladder 80, the distance that axis 26 is spaced apart from platform 60 and/or by restricting the amount of pressurized fluid that can be added to or removed from inflatable bladder 80.

The construction and arrangement of the articles of the patient support device as shown in the preferred and other exemplary embodiments is illustrative only. Although only a few embodiments of the present inventions have been described in detail in this disclosure, those skilled in the art who review this disclosure will readily appreciate that many modifications are possible (e.g. variations in sizes, dimensions, structures, shapes and proportions of the various elements, values of parameters, mounting arrangements, use of materials, colors, orientations, etc.) without materially departing from the novel teachings and advantages of the subject matter recited in the claims. For example, head receiving portion 12 may be configured in a variety of ways to accommodate different portions of the patient's body (e.g., back, legs, arms, etc.). Also, the patient support device may be configured to be permanently coupled to a patient table or other patient support structure. Further, control of the fluid inlet and/or fluid outlet may be controlled by an at least partially automated system so that the operator does not have to physical actuated any of the control mechanisms.

Accordingly, all such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangement of the preferred and other exemplary embodiments without departing from the spirit of the present inventions as expressed in the appended claims.

What is claimed is:

1. A device for supporting a patient during a radiological imaging procedure, the device comprising:
   a base comprising a platform configured to receive an inflatable bladder;
   a support member pivotally coupled to the base and configured to receive a portion of the patient undergoing the radiological imaging procedure; and
   an adjustment device comprising the inflatable bladder, the inflatable bladder being repositionably located on the platform and having a first portion acting on the base and a second portion acting on the support member,
   wherein an inflatable state of the adjustment device is controllable to selectively adjust an angular positioning of the support member between an angle downward relative to the base and an angle upward relative to the base.

2. The device of claim 1 wherein the base comprises at least one projection upwardly extending from the platform, the support member being pivotally coupled to the at least one projection at a position above the platform to permit the support member to pivot to an orientation that is angled downward relative to the base.

3. The device of claim 2 wherein the at least one projection is provided at a front portion of the platform while a rear portion of the platform is configured to receive the inflatable bladder.

4. The device of claim 3 wherein the at least one projection comprises a first projection and a second projection, the first projection being offset from the second projection in a lateral direction, and wherein a pivot shaft extends between the first projection and the second projection, the pivot shaft defining an axis about which the support member is configured to rotate.

5. The device of claim 4 wherein the pivot shaft is integrally molded with the support member as a one-piece, radiolucent, unitary body.

6. The device of claim 1 wherein the support member comprises a support surface that is substantially concave as the support member extends between a first lateral side and a second lateral side.

7. The device of claim 1 wherein the support member comprises a support surface for supporting the patient that curves upwards as the support member extends between a front end and a rear end such that the support surface is concave.

8. The device of claim 7 wherein the support surface comprises a first portion configured to support a neck of the patient and a second portion configured to support a head of the patient.

9. The device of claim 8 wherein the first portion extends in a substantially linear manner as the first portion extends towards the rear end, and wherein the second portion extends in a curved manner as the second portion extends towards the rear end.

10. The device of claim 9 wherein the second portion curves upward with a substantially continuous radius.

11. The device of claim 1 wherein the inflatable bladder is substantially contained within the periphery of the platform.

12. The device of claim 1 wherein the base comprises one of a hook and a loop, and the adjustment device comprises the other of a hook and a loop; and wherein when the inflatable bladder is repositionably located on the platform, the one of a hook and a loop of the base engages the other of a hook and a loop of the adjustment device.

13. A device for supporting a patient during a radiological imaging procedure while on a patient table having a top surface, the device comprising:
   a base including a substantially flat platform having a bottom surface supported by the top surface of the patient table;
   a support member pivotally coupled to the base and configured to receive a portion of the patient undergoing the radiological imaging procedure; and
   an adjustment device comprising an inflatable bladder, the inflatable bladder having a first portion acting on the base and a second portion acting on the support member, the inflatable bladder being substantially contained within a periphery of the platform;
   wherein an inflatable state of the adjustment device is controllable to selectively adjust an angular positioning of the support member relative to the base between an angle upward relative to the top surface of the patient table and an angle downward relative to the top surface of the patient table.

14. The device of claim 13 wherein the device is portable and can be readily removed from the patient table.

15. The device of claim 13 wherein the inflatable bladder is an elongated member having a longitudinal axis extending between a first end wall and a second end wall when inflated, the inflatable bladder including a side wall extending circumferentially around the longitudinal axis, wherein the longitudinal axis is oriented such that is does not intersect the base or the support member such that the side wall is configured to act on the base and the support member.

16. The device of claim 13 further comprising a control mechanism that allows an operator to selectively control the inflatable state of the inflatable bladder by adjusting fluid pressure within the inflatable bladder, the control mechanism comprises a fluid inlet line and a fluid outlet line, the fluid outlet line comprising release valve that can be selectively actuated by the operator.

17. The device of claim 16 wherein the fluid inlet line is configured to be coupled to a pressurized air source for providing pressurized air to the inflatable bladder, and wherein the fluid inlet line comprises a check valve that restricts movement of the pressurized air towards the pressurized air source.

18. The device of claim 13 wherein a cover substantially encloses the inflatable bladder, and wherein the cover is provided with a first fastening element and the platform is provided with a second fastening element, the first fastening element being configured to engage the second fastening element for securing the inflatable bladder to the base.

19. The device of claim 18 wherein the first fastening element is one of a hook and loop fastener and the second fastening element is the other of the hook and loop fastener.

20. A method of adjusting a position of a portion of a patient undergoing a radiological imaging procedure, the method comprising:
   placing a patient support device on top of a patient table, the patient support device comprising a base having a platform configured to be supported by the top of the patient table, a support member and an inflatable bladder for adjusting an angular position of the support member relative to the base;
   placing the portion of the patient undergoing the radiological imaging procedure in the support member; and controlling fluid pressure within the inflatable bladder to selectively rotate the support member between an angle downward relative to the base and an angle upward relative to the base.

21. A device for supporting a patient on a patient table during a radiological imaging procedure, the device comprising:
- a base having a platform configured to be supported by the patient table;
- a support member pivotally coupled to the base and configured to receive a portion of the patient undergoing the radiological imaging procedure; and
- an adjustment device comprising an inflatable bladder, the inflatable bladder having a first portion acting on the base and a second portion acting on the support member,
- wherein an inflatable state of the adjustment device is controllable to selectively adjust an angular positioning of the support member relative to the base between an angle of inclination above horizontal to an angle of inclination below horizontal; and
- wherein the support member comprises a support surface for supporting the patient that curves upwards as the support member extends between a front end and a rear end such that the support surface is concave.

22. The device of claim 21 wherein the platform comprises a substantially flat portion that is configured to support the device on top of the patient table, and wherein the inflatable bladder is substantially contained within a periphery of the platform.

23. A device for supporting a patient during a radiological imaging procedure while on a patient table, the device comprising:
- a base having a platform configured to be supported on top of the patient table;
- a support member pivotally coupled to the base and configured to receive a portion of the patient undergoing the radiological imaging procedure; and
- an adjustment device comprising an inflatable bladder, the inflatable bladder being an elongated member having a longitudinal axis extending between a first end wall and a second end wall when inflated, the inflatable bladder including a side wall extending circumferentially around the longitudinal axis, wherein the longitudinal axis is oriented such that is does not intersect the base or the support member such that a first portion of the side wall acts on the base and a second portion of the sidewall acts on the support member; and
- wherein an inflatable state of the adjustment device is controllable to selectively adjust an angular positioning of the support member between an angle downward relative to the base and an angle upward relative to the base.

24. The device of claim 23 wherein the longitudinal axis of the inflatable bladder extends substantially horizontally.

* * * * *